United States Patent [19]
Teunissen et al.

[11] Patent Number: 5,811,589
[45] Date of Patent: Sep. 22, 1998

[54] PROCESS FOR THE PREPARATION OF A LINEAR ALDEHYDE ORGANIC COMPOUND

[75] Inventors: Antonius J. J. M. Teunissen, Geleen; Johannes G. De Vries, Maastricht; Onko J. Gelling, Geleen, all of Netherlands; Cornelis Lensink, Avalon, New Zealand

[73] Assignee: DSM N.V., Netherlands

[21] Appl. No.: 552,851

[22] Filed: Nov. 3, 1995

Related U.S. Application Data

[63] Continuation of PCT/NL94/00093, Apr. 29, 1994.

[30] Foreign Application Priority Data

| May 6, 1993 | [BE] | Belgium | 9300464 |
| May 6, 1993 | [BE] | Belgium | 9300514 |

[51] Int. Cl.$^6$ .................................................. C07C 45/00
[52] U.S. Cl. ............................................ 568/451; 568/454
[58] Field of Search ...................................... 568/451, 454

[56] References Cited

U.S. PATENT DOCUMENTS

| 3,996,293 | 12/1976 | Knifton et al. . |
| 4,593,126 | 6/1986 | Cornils et al. . |
| 4,795,727 | 1/1989 | Bach et al. . |
| 4,801,738 | 1/1989 | Schneider et al. . |
| 4,849,542 | 7/1989 | Drent . |
| 4,879,418 | 11/1989 | Bach et al. . |

FOREIGN PATENT DOCUMENTS

| A1 0 125 567 | 11/1984 | European Pat. Off. . |
| 2627354 | 12/1976 | Germany . |
| 1368434 | 9/1974 | United Kingdom . |

*Primary Examiner*—Paul J. Killos
*Attorney, Agent, or Firm*—Cushman Darby & Cushman IP Group of Pillsbury Madison & Sutro, LLP

[57] ABSTRACT

Process for the preparation of a linear aldehyde organic compound by hydroformylation (b) starting from an internally unsaturated functionalised organic compound whereby first (a) a portion of the internally unsaturated functionalized organic compound is isomerized to a terminally unsaturated functionalised organic compound in the presence of a suitable isomerization catalyst, wherein following the isomerization step (a), the hydroformylation (b) is effected in the presence of carbon monoxide, hydrogen and a catalyst which preferentially catalyzes the hydroformylation reaction of the terminally unsaturated functionalised organic compound to the linear aldehyde organic compound, the internally unsaturated functionalised organic compound remaining practically unhydroformylated, whereupon (c) the linear aldhyde organic compound is separated out of the mixture and (d) the remainder of the unsaturated functionalised organic compound-containing mixture is recirculated to the isomerization step (a).

31 Claims, 1 Drawing Sheet

PROCESS FOR THE PREPARATION OF A LINEAR ALDEHYDE ORGANIC COMPOUND

RELATED APPLICATIONS

This is a continuation of PCT International Application PCT/NL 94/00093 filed Apr. 29, 1994.

BACKGROUND OF THE INVENTION

The invention relates to a process for the preparation of a linear aldehyde organic compound by hydroformylation (b) starting from an internally unsaturated functionalized (substituted with a functional group) organic compound whereby first (a) a portion of the internally unsaturated functionalized organic compound is isomerized to a terminally unsaturated functionalised organic compound in the presence of a suitable isomerization catalyst.

Such a process is disclosed in U.S. Pat. No. 4,801,738. In that patent specification, a process is described for the preparation of a 5-formylvalerate starting from the corresponding 3-pentenoate (the 3-pentenoate is an internally unsaturated functionalized organic compound because the C=C-bond is bonded with two carbon atoms on each carbon atom of the C=C portion. 4-pentenoate is in contrast a terminally unsaturated functionalized organic compound). First, the 3-pentenoate is partly isomerized to the 4-pentenoate. Subsequently, the 4-pentenoate is separated out of the pentenoate mixture, containing mostly 3-pentenoate, in a distillation column with 100 separation stages and at a reflux ratio of 50. Next, the resulting 95-% pure 4-pentenoate is hydroformylated with high selectivity to the 5-formylvalerate in the presence of a rhodium-triphenylphosphine ligand catalyst.

A disadvantage of this known process is that it is difficult to achieve virtually complete separation of the terminally unsaturated functionalized organic compound out of the mixture of terminally and internally unsaturated functionalized organic compounds by distillation because the boiling points of these isomers are as a rule are close together. That such a separation is difficult to achieve is described in for instance DE-A-3412295 and also appears from the large number of separation stages and the high reflux ratio of the distillation column referred to above.

When such a distillation is omitted the selectivity in the hydroformylation step towards the linear aldehyde organic compound is relatively low, resulting in the formation of a significant amount of the branched aldehydes (linear: meaning that the formyl group is in for example the formylvalerate molecule on the 5-position of the valerate molecule and thus forming a linear chain of carbon atoms; branched: meaning that the formyl group is in this case on the 3 or 4 position and thus not forming a linear chain of carbon atoms). The ratio between linear aldehyde organic compound and the total of branched aldehydes is referred to as the n/i ratio. Selectivity is defined as the molar amount of the specific aldehyde product on the total of aldehyde products and hydrogenated starting compound. The hydrogenated starting compound (methylvalerate in case of pentenoate) is the most important byproduct of the hydroformylation reaction according to the invention.

SUMMARY OF THE INVENTION

Figure 1:
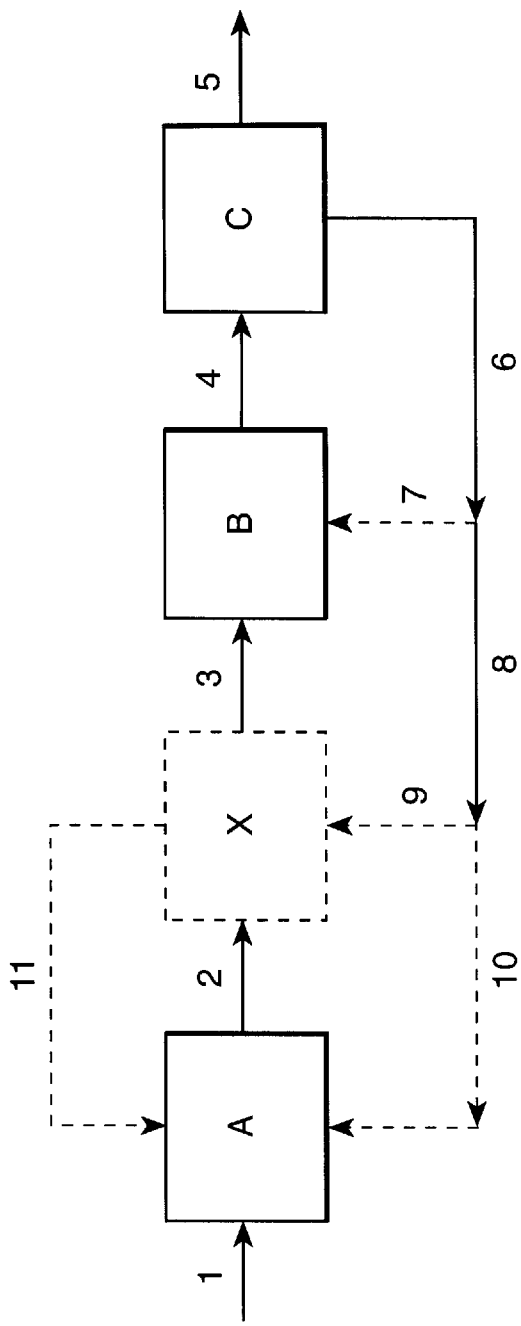
FIG. 1 represents a process embodiment of the invention.

Accordingly, the object of the present invention is to provide a process by which linear aldehyde organic compound can be prepared with a high n/i ratio and a high selectivity.

This object is achieved in that, following the isomerization step (a), the hydroformylation (b) is effected in the presence of carbon monoxide, hydrogen and a catalyst which preferentially catalyzes the hydroformylation reaction of the terminally unsaturated functionalized organic compound to the linear aldehyde organic compound, the internally unsaturated functionalized organic compound remaining practically unhydroformylated, whereupon (c) the linear aldehyde organic compound is separated out of the mixture and (d) the remainder of the unsaturated functionalized organic compound-containing mixture is recirculated to the isomerization step (a).

DETAILED DESCRIPTION OF THE INVENTION

When the preparation of a linear aldehyde organic compound is effected in accordance with the invention, it is found that virtually complete separation of the terminally unsaturated functionalized organic compound from the mixture leaving the isomersization step (a) is not necessary for preparing the linear aldehyde organic compound with a high selectivity. This separation of the terminally- and internally unsaturated functionalized organic compound may be omitted or may be effected with a low separating power. An advantage of separation with a low separating power is that the mixture becomes richer in terminally unsaturated functionalized organic compounds while the separation itself does not have to be very complicated. For example when using a distillation process with only a few separation stages and a lower reflux ratio compared to the process according to U.S. Pat. No. 4,801,738 is sufficient.

Any internally unsaturated functionalized organic compound capable of forming a terminally unsaturated functionalized organic compound through isomerization is a suitable starting material for the process according to the invention.

The internally unsaturated compound may be functionalized with an alcohol-, aldehyde-, ester-, carboxylic acid- or nitrile group. The organic compound may have 4 to 30 carbon atoms. Examples of suitable starting compounds are 2-butenal, 2-butenol, 3-pentenenitril, 3-pentenal, 3-pentenol and 4-hexenal. Particularly suitable are esters and carboxylic acids represented by the following chemical formula:

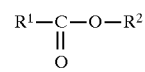

where $R^1$ represents a branched or unbranched acyclic hydrocarbon group having one or more internal double bonds with 3 to 11 carbon atoms and $R^2$ represents hydrogen atom or an alkyl group with 1 to 8 carbon atoms or an aryl group or arylalkyl group with 6 to 12 carbon atoms.

It is preferred that $R^1$ is an internally unsaturated hydrocarbon group having 4 carbon atoms. These pentenoate or pentenoic acid compounds are preferred starting compounds because the resulting 5-formylvalerate or 5-formylvaleric acid can serve as starting material in the preparation of caprolactam, caprolactone and adipic acid.

Suitable pentenoates are alkyl pentenoates in which the alkyl group has from 1 to 8 carbon atoms. A suitable alkyl group is the methyl-, ethyl-, propyl-, isopropyl-, n-butyl-, isobutyl- or the cyclohexyl group. Another group of suitable pentenoates are aryl pentenoates or arylalkyl pentenoates in which the aryl group or arylalkyl group has from 6 to 12 carbon atoms. A suitable aryl group is the phenyl group and a suitable arylalkyl group is the benzyl group.

The mixture which, besides the recirculated unconverted unsaturated organic compounds of step (d), is fed to the isomerization step (a) may contain, besides the internally unsaturated organic starting compound, an amount of terminally unsaturated functionalized organic compound. When starting from pentenoate this mixture will generally consist primarily of the 3-pentenoate and, optionally, small amounts of 2- and/or 4-pentenoate. The pentenoate mixture can for example be prepared by carbonylation of butadiene.

The internally unsaturated functionalized organic compound may be isomerized to the terminally unsaturated functionalized organic compound in the presence of an isomerization catalyst in any known manner. Techniques for isomerizing olefins are to be found in for instance: H. N. Dunning, Ind. Eng. Chem., 1953, 45, 551–564, J. E. Germain, "Catalytic conversion of hydrocarbons", Academic press, 1969, H. Pines, W. M. Stalick, "Base catalyzed reactions of hydrocarbons and related compounds", Academic press, 1977, M. Orchin, Adv. Catal., 1966, 16, 2–47 and in A. J. Hubert and H. Reimlinger, Synthesis, 1970, 405–30. Suitable isomerization catalysts may be subdivided into metallic and organometallic isomerization catalysts.

Suitable isomerization catalysts are for instance homogeneous metal-based catalysts in combination with one or more inorganic or organic ligands capable of either adding to the olefin as hydride compound or forming n-alkyl complexes. Examples of such catalysts are: $WCl_6$-$Bu_4Sn$, $Pd(OAc)_2$ (HOAc=acetic acid), Pd(II), $Fe(CO)_5$, $Fe(CO)_{12}$, $Co_2(CO)_8$, $TiCl_3$-$Et_3Al$, $VCl_3$-$Et_3Al$, $HCoN_2(P(Ph)_3)_3$, $HCo(PPh_3)_3$, $HCo[P(OPh)_3]_4$, $HRu(PPh_3)_3Cl$, $HRu(CO)(PPh_3)_3Cl$, $M(CO)_4L_2$ (M=Cr, Mo, W), $Ni[P(OEt)_3]_4/CF_3COOH$, $K_2[HPt(SnCL_3)Cl_2]$, $MCl_n$ (M=Cr, Mn, Fe, Co, Ni, Cu, Zn, n=valency), $MX_2$-$AlEt_3$ (M=Fe, Co or Ni; X=Cl or acac) where Bu=butyl, Pr=propyl, Ph=phenyl, Et=ethyl, acac=acetyl acetonate. These catalysts may also be immobilized on a fixed carrier such as an ion exchanger or a paracrystalline compound such as a variety of zeolites, clay, silica and alumina carriers. Other suitable catalysts include (noble) metals on a carrier (Ziegler-Natta catalysts).

Especially suitable isomerization catalysts for the isomerization of 3-pentenoate (and optionally 2-pentenoate) to the 4-pentenoate are described in for instance EP-A-343.598, EP-A-291.033, EP-A-266.689, DE-A-3.521.380, DE-A-3.521.381 and DE-A-3.317.163. With regard to the reaction conditions of the isomerization step, the reader is referred to the aforementioned patent specifications. As a rule, the mixture leaving the isomerization step (a) contains the following isomeric pentenoates: 3–12% 4-pentenoate, 75–95% 3-pentenoate and 0–10% 2-pentenoate.

It may be advantageous to distill the mixture of internally and terminally unsaturated functionalized organic compounds so as to enrich the mixture with respect to the terminally unsaturated compound. It suffices to use a distillation column with few separation stages and a normal reflux ratio because the invention does not call for virtually pure terminally unsaturated functionalized organic compound (such as the 95% pure 4-pentenoate in U.S. Pat. No. 4,801,738). After being liberated of the terminally unsaturated functionalized organic compound in the distillation step, the mixture, substantially consisting of internally unsaturated organic compounds, is preferably recirculated to the isomerization step (a). An advantage of the enrichment is that the reactor volume used for the hydroformylation can be kept limited. It will be clear that this enrichment in terminally unsaturated organic compounds need not necessarily be effected by distillation. Other separation techniques such as crystallization, absorption and the like are also possible. A typical mixture of for example pentenoates led to the hydroformylation (b) contains 3–90 wt. % 4-pentenoate (relative to the total of pentenoates). The mixture preferably contains more than 20% 4-penteroate because, otherwise, the required hydroformylation reactor volume would be very large. The mixture preferably contains less than 90% and most preferably less than 80% 4-pentenoate because, in that case, the distillation can be carried out in a simple manner.

The hydroformylation in step (b) must be carried out in the presence of a suitable catalyst. This catalyst is characterized in that this catalyst preferentially catalyzes the hydroformylation reaction of the terminally unsaturated functionalized organic compound to the linear aldehyde organic compound and hardly catalyzes the hydroformylation of the internally unsaturated functionalized organic compounds present in the mixture. Preferentially here means that the reaction rate constant of the conversion of the terminally unsaturated functionalized organic compound is more than 50 times the reaction rate constant of the conversion of the internally unsaturated functionalized organic compound. Preferably, the reaction rate constant of the terminally unsaturated functionalized organic compound is more than 100 times, more preferably more than 200 times the reaction rate constant of the internally unsaturated functionalized organic compound.

Such a catalyst is described in for instance U.S. Pat. No. 3,996,293, to which the reader is referred for the sake of brevity. The catalysts described in U.S. Pat. No. 3,996,293 are ligand-stabilized platinum(II)-dihalide complexes in combination with Group IVb metal halides such as $PtCl_2[P(C_6H_5)_3]_2$-$SnCl_2$. With such a catalyst it is possible to hydroformylate for example, a mixture comprising a 4-pentenoate and at least one other isomeric pentenoate according to the invention to the 5-formylvalerate with 80% conversion (97% selectivity), less than 1% of the internally unsaturated pentenoate present being converted (ratio=1:1). The use of this catalyst in a process according to the invention not only provides a more simplier process but also provides a process with a higher selectivity compared to the process of U.S. Pat. No. 4,801,738.

A second suitable class of hydroformylation catalysts for the process according to the invention includes combinations of a cationic platinum complex and a suitable bidentate phosphine in a polar solvent. The use of such catalysts for the hydroformylation of olefins in the presence of $SnCl_2$ and/or a protic acid is known (J. of Organometallic Chemistry, 417 (1991) C41–C45). It has been found that, if $SnCl_2$ and the protic acid are omitted, this catalyst system preferentially catalyzes the hydroformylation reaction of for example 4-pentenoate in a mixture of at least one other pentenoate whilst this other pentenoate remains practically unconverted. A suitable bidentate phosphine is 1,4-bis-diphenylphosphinobutane. Suitable solvents are ketones such as butanone and acetone.

The most preferred embodiment of the invention is to perform the hydroformylation at elevated pressure and temperature in the presence of rhodium and a triphenylphosphine wherein the triphenylphosphine is substituted with functional groups such that the substituted triphenylphosphine is water-soluble and the reaction is carried out in the presence of water.

It has been found that, if such a triphenyl-phosphine is applied, the selectivity towards the linear aldehyde organic compound such as for example 5-formylvalerate is higher than the selectivity attained with the process described in U.S. Pat. No. 4,801,738.

An added advantage when using this catalyst is that the catalyst can be separated from a reaction mixture, which does not mix with water, more easily than compared to the process described in the aforementioned U.S. Pat. No. 4,801,738. This separation can be readily accomplished by phase separation of the water phase, in which the rhodium and the subsituted triphenylphosphine are dissolved, and the organic phase, in which the reaction products are present. A reaction mixture which does not mix with the water phase is present when 5-formylvalerate is prepared. For this reason it is extra advantageous to perform the hydroformylation in the above described embodiment when preparing 5-formylvalerate.

Suitable triphenylphosphines according to this embodiment of the invention are so substituted with functional groups that the triphenylphosphine is soluble in water. Examples of suitable substituted functional groups are sulphonate groups, carboxylate groups and cationic residual groups of ammonium salts.

Such triphenylphosphines may be represented by the following general chemical formulae:

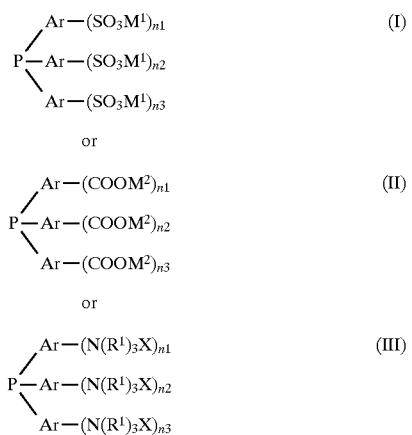

where Ar represents a phenyl group, $M^1$ and $M^2$ represent idependently of each other a cationic organic or inorganic radical, X independently of each other represents an anionic organic or inorganic radical, $R^1$ independently of each other represents an aliphatic hydrocarbon group with 1 to 18 carbon atoms and n1, n2 and n3 may, independently, be 0 or 1, the sum of n1, n2 and n3 being greater than or equal to 1.

The phosphines according to the invention may be applied in pure form in which n1, n2 or n3 equal 1, 2 or 3 or as a mixture of triphenylphosphines, in which the sums of n1, n2 and n3 for the various triphenylphosphines of the mixture are unequal to one another. The application of such a mixture is advantageous inasmuch as this mixture is formed in the preparation of substituted triphenylphosphines so that further purification may be omitted. Preferably, in such a mixture, the average sum of n1, n2 and n3 of the substituted triphenylhosphines is greater than 2.5. More preferably, this sum is greater than 2.8.

Suitable cationic radicals ($M^1$ or $M^2$) are the inorganic cations of metals, notably of alkali metals and earth alkali metals such as sodium, potassium, calcium and barium as well as ammonium ions or quaternary ammonium ions such as tetramethyl ammonium, tetrapropyl ammonium or tetrabutyl ammonium.

Suitable anionic radicals (X) are the sulphate and phosphate groups and organic acid radicals such as $R^2\text{-}SO_3^-$, $R^2\text{-}CO_2^-$ and $R^2\text{-}PO_3^-$, where $R^2$ represents a $C_1$–$C_{12}$ alkyl or a $C_1$–$C_{12}$ aryl.

It is preferred for the carboxylate groups (see formula II) and the cationic radicals of ammonium salts (formula III) to be para-substituted and for the sulphonate groups (formula I) to be meta-substituted on the phenyl group.

Examples of such substituted triphenylphosphines are (monosulphonatophenyl)diphenyl phosphine, di(monosulphenatophenyl) phenyl phosphine, tri (monosulphonatophenyl)phosphine, (monocarboxyphenyl) diphenyl phosphine, di(monocarboxyphenyl)phenyl phosphine and tri(monocarboxyphenyl)phosphine.

The preparation of a triphenylphosphine according to formula I is described in, for instance, an article by G. P. Schiemenz & H. U. Siebeneick, Chem. Ber. 1969, 102, 1883–91.

The preparation of a triphenylphosphine substituted with a substituted ammonium salt (formula III) is described in, for instance, U.S. Pat. No. 4,522,932.

The application of a triphenylphosphine with sulphonate groups as a ligand (as in the present invention) in hydroformylating an alkene with rhodium is known per se from DE-A-2.627.354. That patent specification sets out that such a catalyst may be utilized for the hydroformylation of both internal unsaturated alkenes, such as 2-butene, 2-pentene and 3-octene, and terminally unsaturated alkenes such as propene, 1-butene and 1-pentene. Moreover unsaturated functionalized organic compounds are not mentioned as possible starting materials. It is surprising, then, that, in applying such a catalyst during the hydroformylation of a mixture terminally- and internally unsaturated functionalized organic compounds, the terminally unsaturated compound is converted to aldehydes whilst the internally unsaturated compound remains practically unconverted.

Rhodium may be applied in various forms. The manner in which rhodium is introduced into the reaction mixture is not very critical. Suitable rhodium compounds are water-soluble compounds and rhodium compounds which become water-soluble under the reaction conditions. As a rule, the catalytically active complexes that are based on a rhodium precursor, such as $Rh(CO)_2$-acetyl-acetonate (acetylacetonate=acac), $Rh_2O_3$, $Rh_4(CO)_{12}$, $Rh_6(CO)_{16}$, $Rh(NO_3)_2$, $Rh(OAc)_2$ (AcOH=acetic acid) and the substituted triphenylphosphine are formed in the reaction mixture. Preferably, $Rh(CO)_2$-acetylacetonate or $Rh(OAc)_2$ is used as rhodium precursor, this precursor forming a precursor of the active complex in a solvent in combination with the substituted triphenylphosphine. This complex subsequently reacts with excess ligand (the substituted triphenylphosphine) in the reaction mixture to form the catalytically active complex.

The hydroformylation may be effected in the presence or absence of an extra solvent besides water. Besides the solvent, the reaction mixture will generally also contain an amount of high-molecular-weight by-products, methyl valerate and condensation products, which are kept in circulation together with an amount of unconverted pentenoate.

Examples of suitable solvents are ketones such as acetophenone and cyclohexanone; ethers for example diethylether, anisol and diphenylether; aromatic compounds for example benzene, toluene and xylene; paraffins for example hexane, heptane, cyclohexane, methylcyclohexane and iso-octane and esters for example methylbenzoate and methylvalerate. Preferably, aromatic and/or paraffinic solvents are applied. Mixtures of solvents may also be applied.

The weight ratio between the organic phase (pentenoate+ solvent (if used)): water generally is between 10:90 and 90:10.

The weight ratio between water: pentenoate generally is between 10:90 and 90:10.

The pH of the water phase generally is between 5.8 and 10. The pH of the water phase during hydroformylation is preferably not higher than 8.5 because otherwise the ester group may hydrolyse.

The (carbon monoxide/hydrogen) pressure generally is between 0.1 and 10 MPa. Preferably, the pressure is between 0.2 and 5 MPa.

The molar ratio between carbon monoxide: hydrogen generally is between 1:4 and 4:1. This ratio will preferably be between 1:1 and 1:2.

The temperature generally is between 40° and 150° C. and preferably between 80° and 120° C.

The rhodium concentration in the reaction mixture generally is between 50–700 ppm.

The molar ratio rhodium of: substituted triphenylphosphine is between 1:10 and 1:2000. Preferably between 1:40 and 1:200.

The two phase reaction mixture (if present) should be well agitated to achieve a suitable contact between the reaction compounds and the catalyst. Preferably the reaction mixture is stirred. Static mixers are also suitable.

In step (c), the linear aldehyde organic compound is separated from the mixture leaving the hydroformylation step (b). In general, the pentenoate is separated by distillation prior to the lineair aldehyde organic compound being recovered by distillation. Any impurities that may have formed can be removed in this step also. On being isolated, by-products such as branched aldehydes may optionally be catalytically cracked to form a unsaturated functionalized organic compound as described in EP-A-295.549.

In step (d), the mixture freed of linear aldehyde organic compound is recirculated to step (a). This mixture will generally contain internally unsaturated functionalized organic compound and may or may not contain some incompletely converted terminally unsaturated organic compound.

A process embodiment according to the invention can be described with reference to FIG. 1.

A mixture containing internally unsaturated functionalized organic compound is led to step A through stream 1. In step A, isomerization takes place, with a portion of the internally unsaturated functionalized organic compound isomerizing to the terminally unsaturated functionalized organic compound. The terminally unsaturated functionalized organic compound-containing mixture is conveyed to step B through lines 2 and 3. The mixture is optionally enriched with a terminally unsaturated functionalized organic compound in distillation step X, the stream that is recirculated to isomerization step A via line 11 substantially consisting of an internally unsaturated functionalized organic compound. Hydroformylation takes place in step B, the terminally unsaturated functionalized organic compound being preferentially converted to the linear aldehyde. The aldehyde-containing mixture is lead to step C with stream 4. In step C, the aldehyde is separated out and discharged with stream 5. The internally unsaturated functionalized organic compound and any unconverted terminally unsaturated functionalized organic compounds are recirculated to step A through lines 6-8-10. This recirculating stream may optionally be lead to distillation step X through lines 6-8-9 in order for unconverted terminally unsaturated functionalized organic compound to be separated out and sent to the hydroformylation through line 3. The remaining mixture, substantially consisting of internally unsaturated functionalized organic compound, goes to the isomerization step A through line 11. It may also be advantageous to return a portion of the mixture in line 6 straight to the hydroformylation via line 7 and to recirculate the remainder to step A and/or step X through line 8.

The invention is also directed to solely the hydroformylation of a mixture comprising 4-pentenoate and at least one other isomeric pentenoate to 5-formylvalerate in which triphenylphosphine is used, in which the triphenylphosphine being so substituted with functional groups that the substituted triphenylphosphine is water-soluble and the reaction being carried out in the presence of water as described above. The hydroformylation of 4-pentenoate to 5-formylvalerate according to this embodiment of the invention is advantageous because the reaction mixture, consisting of substrate and products, can be easily separated from the catalyst and because the 5-formylvalerate can be prepared with a high selectivity and n/i ratio.

The 4-pentenoate may be hydroformylated in the presence of a 3- and/or 2-pentenoate. A mixture of 2-, 3- and 4-pentenoates may be prepared starting from, for instance, the 3-pentenoate. This can involve isomerization of the 3-pentenoate in the presence of an isomerization catalyst as described above. The 2-pentenoate content of a mixture after isomerization preferably is between 0–2%. Another possible process to prepare a suitable mixture of pentenoates which can be hydroformylated with this catalyst is carbonylation of butadiene in the presence of an alcohol. This mixture can for example be directly hydroformylated with the process according to the invention or can be subjected to an isomerization and/or a destillation.

Since in the process according to the invention the 3-pentenoate and also the 2-pentenoate remain practically unconverted by hydroformylation in comparison with the 4-pentenoate, it is not necessary to separate these components prior to hydroformylation. Nevertheless, it may be advantageous to enrich the mixture in 4-pentenoate so that the required hydroformylation reactor volume can be limited. This separation calls for distillation using a few separation stages and a normal reflux ratio rather than a column with 100 separation stages and a reflux ratio of 50 as mentioned in U.S. Pat. No. 4,801,738.

The reaction conditions described above for this catalyst are also valid for this embodiment of the invention. The compositions for the mixture of pentenoates which are described earlier are also valid for this embodiment of the invention.

The invention is elucidated by the following non-limiting examples.

EXAMPLE I

A 150-ml Hastalloy-C autoclave (Parr) was filled under nitrogen with 5.7 mg of $Rh(CO)_2acac$ (acac=acetylacetonate) and 30 ml of aqueous solution containing 70.76 mmol/l tris-(m-sulphonatophenyl) phosphine as sodium salt (TPPTS). The autoclave was closed and purged with nitrogen. Hereafter, the autoclave was heated to 110° C. in approx. 10 min. and subsequently pressurized to 1.0 MPa using $CO/H_2$ (1:1). A mixture of methyl 3-pentenoate (3.29 g), methyl 4-pentenoate (0.69 g) and n-nonane (internal standard, 0.49 g) in 19 g of toluene was pressure-injected into the autoclave. During the reaction, a pressure of 1.0 MPA and a temperature of 110° C. were maintained while the autoclave was stirred at 1200 rpm. The composition was checked at regular intervals through GLC. The results are given in Table 1.

EXAMPLES II–VIII

These examples were carried out in the same way as Example I, the ratio between methyl 3- and 4-pentenoate and the ratio between ligand and rhodium being varied, the total amount of methylpentenoate and rhodium (except in Examples V and VI) being equal to the amounts in Example I. The water/toluene ratio (V/V) were equal to 1. In examples VI and VI the addition of toluene was omitted and some more of the mixture of methyl 3- and 4-pentenoate was added so that the total volume of pentenoates amounted to 30 ml. The results are given in Table 1.

COMPARATIVE EXPERIMENT A

Example I was repeated except that 1.24 g of triphenylphosphine ($Ph_3P$) was used as ligand and no water was used. The reaction was carried out using a mixture of methyl-3-pentenoate (4.51 g) and methyl 4-pentenoate (0.62 g).

EXAMPLE VII

The isomerization of the methyl 3-pentenoate (step a) was carried out by stirring a mixture of 50 g of methyl 3-pentenoate and 5 g of a zeolite catalyst of the Y type, which catalyst contains 0.5 wt. % palladium, in a glass vessel at 135° C. for 360 seconds. The resulting reaction mixture contained 4 g of methyl 4-pentenoate, 0.05 g of methyl cis 2-pentenoate and 0.1 g of methyl trans 2-pentenoate and 45.8 g of methyl 3-pentenoate. After the catalyst had been separated out, the mixture was distilled in a "Spalt" distillation column (25 separation stages) at 250 mbar and a reflux ratio of 20. Distillation was continued until 7.7 grams of a mixture of methylpentenoate had separated out at the top of the column. This mixture contained 49% methyl 4-pentenoate. The remaining (bottom) mixture was returned to the isomerization step.

The hydroformylation (step b) was carried out with 4 g of the mixture obtained by the distillation by repeating Example 1 at 140° C. The results of the hydroformylation are given in Table 1.

EXAMPLE VIII

Example I was repeated with $P(C_6H_4\text{-p-}CO_2Na)_3$ (Table 1: $At_3P$), the ratio between methyl 3- and 4-pentenoate and the ratio between ligand and rhodium being varied, the total amount of methylpentenoate and rhodium being equal to the amounts in Example I.

TABLE 1

| Example | Ligand | Lig/Rh (1) | Me3p:Me4p (2) | Time (h) | Conversion Me3p | Conversion Me4p (3) | Sel n-ald (%) (4) | n/i ratio (5) |
|---|---|---|---|---|---|---|---|---|
| I | TPPTS | 96 | 83:17 | 2.43 | 0.0 | 44 | 87 | 7.9 |
| | | | | 5.72 | 0.0 | 81 | 84 | 6.4 |
| II | TPPTS | 150 | 50:50 | 1.50 | 0.0 | 34 | 95 | 18.2 |
| | | | | 3.00 | 0.0 | 45 | 95 | 19.7 |
| | | | | 6.00 | 0.0 | 69 | 95 | 21.0 |
| III | TPPTS | 145 | 71:29 | 1.50 | 0.0 | 33 | 95 | 18.0 |
| | | | | 3.00 | 0.0 | 53 | 95 | 17.8 |
| | | | | 6.00 | 0.0 | 67 | 94 | 15.9 |
| IV | TPPTS | 145 | 95:5 | 3.00 | 0.0 | 49 | 90 | 12.4 |
| | | | | 6.00 | 0.0 | 65 | 93 | 12.6 |
| V (7) | TPPTS | 145 | 50:50 | 6.00 | 0.0 | 85 | 94 | 17.4 |
| VI (6,8) | TPPTS | 40 | 50:50 | 0.50 | 0.0 | 52 | 94 | 17.0 |
| | | | | 0.85 | 0.0 | 79 | 93 | 15.0 |
| VII (9) | TPPTS | 148 | 51:49 | 1.00 | 0.0 | 50 | 92 | 16.0 |
| | | | | 3.50 | 0.0 | 67 | 92 | 15.9 |
| | | | | 6.00 | 0.0 | 94 | 90 | 12.5 |
| VIII | $Ar_3P$ | 152 | 50:50 | 0.83 | 0.0 | 12 | 94 | 14.3 |
| | | | | 6.15 | 0.0 | 36 | 92 | 13.7 |
| | | | | 9.00 | 0.0 | 50 | 91 | 13.6 |
| Exp. A | $PH_3P$ | 157 | 88:12 | 0.17 | 4.1 | 31 | 60 | 1.5 |
| | | | | 0.59 | 7.3 | 73 | 56 | 1.3 |
| | | | | 1.85 | 18.8 | 98 | 38 | 0.6 |

TABLE 2

| Example | Ligand | Lig/Pt | Me3p/Me4p | Time (h) | Conversion Me3p | Conversion Me4p | Sel n-ald (%) | n/b |
|---|---|---|---|---|---|---|---|---|
| IX | $Ph_2P(CH_2)_4PPh_2$ | 1 | 50:50 | 4.00 | 0 | 97 | 71 | 7.8 |

(1): ligand/rhodium molar ratio
(2): methyl 3-pentenoate:methyl 4-pentenoate molar ratio
(3): conversion (%) of methyl 3-pentenoate and of methyl 4-pentenoate
(4): selectivity of normal aldehyde product (%)
(5): ratio of normal product to iso-aldehyde product
(6): $H_2/CO$ = 2 (mole/mole)
(7): Toluene was omitted
(8): 16 mg $Rh(CO)_2acac$
(9): Temperature = 140° C.

EXAMPLE IX

A solution of $(COD)Pt(Acac)BF_4$ (83 mg) and 1,4-bis-(diphenylphosphino)-butane (74 mg) in 40 ml of butanone was transferred into a Hastalloy-C autoclave (Parr) under nitrogen. After the autoclave had been purged three times with 30-bar $H_2/CO$ (1:1), the solution was heated under the same pressure to 100° C. A solution of methyl 3-pentenoate (0.90 g), methyl 4-pentenoate (0.94 g) and n-nonane (internal standard, 1.02 g) in 5 ml of butanone was pressure-injected into the autoclave, whereupon the pressure was brought to 80 bar $CO/H_2$ (1:1). The reaction was terminated after it had proceeded for four hours at 80 bar and 100° C. with stirring at 1200 rpm. The reaction components were analyzed through GLC. The results are given in Table 2.

Comparison of the results of Examples I–VIII and Comparative Experiment A shows that the application of sulphonated or carboxylated triphenylphosphine makes it possible to selectively convert 4-pentenoate into a 5-formylvalerate from a mixture of 2-, 3- and 4-pentenoates whilst the conversion is less selective when an unsubstituted triphenylphosphine is applied as ligand. It has also been found that, in the same conversion of the methyl 4-pentenoate, the n/i ratio and the selectivity towards formylvalerates are markedly better if the sulphonated triphenylphosphine is used as ligand in the hydroformylation.

Example IV shows that a typical mixture of alkyl 3- and 4-pentenoates can be directly hydroformylated with high selectivity after isomerization of an alkyl 3-pentenoate, without an enrichment (through distillation) of the alkyl 4-pentenoate as described in U.S. Pat. No. 4,801,738 being necessary.

Example VII shows that, starting from methyl 3-pentenoate it is possible to obtain a linear aldehyde with a high selectivity by applying an isomerization step, simple distillation and hydroformylation in accordance with the invention.

We claim:

1. A process for preparing a linear aldehyde compound comprising the steps of:
   (i) forming an isomeric mixture of internally and terminally unsaturated organic compounds by isomerization of an internally unsaturated organic compound,
   (ii) hydroformylating the terminally unsaturated organic compound in the presence of a catalyst which is capable of selectively catalyzing hydroformylation of the terminally unsaturated organic compound, under conditions such that a linear aldehyde compound is formed and there is substantially no hydroformylation of the internally unsaturated organic compound by the catalyst, and
   (iii) recovering the linear aldehyde compound.

2. The process according to claim 1, which further comprises the step of recirculating any remaining isomeric mixture to step (i) and repeating steps (i) to (iii).

3. The process according to claim 1, wherein the catalyst catalyzes hydroformylation of the terminally unsaturated organic compound at a reaction rate constant which is more than 50 times the reaction rate constant at which the catalyst catalyzes the hydroformylation of the internally unsaturated organic compound.

4. The process according to claim 1, wherein the catalyst catalyzes hydroformylation of the terminally unsaturated organic compound at a reaction rate constant which is more than 100 times the reaction rate constant at which the catalyst catalyzes the hydroformylation of the internally unsaturated organic compound.

5. The process according to claim 1, wherein the internally unsaturated organic compound contains between 4 and 30 carbon atoms and carries a functional group selected from the group consisting of an alcohol, aldehyde, ester, carboxylic acid and nitrile group.

6. The process according to claim 1, wherein the internally unsaturated organic compound has the formula

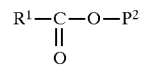

wherein $R^1$ represents a $C_{3-11}$ branched or unbranched acyclic hydrocarbon group having one or more internal double bonds, and $R^2$ represents a hydrogen atom, $C_{1-8}$ alkyl group, aryl group, or $C_{6-12}$ arylalkyl group.

7. The process according to claim 6, wherein the organic compound is a pentenoate.

8. The process according to claim 7, wherein the pentenoate is an alkyl pentenoate and the alkyl group contains between 1 and 8 carbon atoms.

9. The process according to claim 8, wherein the isomeric mixture comprises 3-pentenoate and 5–90% 4-pentenoate.

10. The process according to claim 9, wherein the isomeric mixture comprises 20–80% 4-pentenoate.

11. The process according to claim 1, wherein the catalyst consists essentially of a platinum complex and a bidentate phosphine in a solvent, in the absence of $SnCl_2$ and protic acid.

12. The process according to claim 1, wherein the hydroformylation is carried out in the presence of water, rhodium and a water soluble, substituted triphenylphosphine.

13. The process according to claim 12, wherein the triphenylphosphine is represented by at least one of the following formulas:

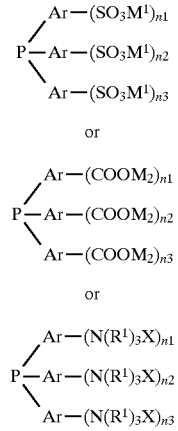

wherein Ar represents a phenyl group, $M^1$ and $M^2$ represent a cationic organic or inorganic radical, X represents an anionic organic or inorganic radical, R represents an $C_{1-18}$ aliphatic hydrocarbon group, n1, n2 and n3 are the same or different and are each 0 or 1, and the sum of n1, n2 and n3 is at least 1.

14. The process according to claim 13, wherein $SO_3M^1$ is meta-substituted and $COOM_2$ or $N(R^1)_3X$ are para-substituted at a phenyl group.

15. A process for the preparation of 5-formylvalerate by hydroformylation of 4-pentenoate which is present in a mixture with at least one other isomeric pentenoate, in the presence of water, rhodium and a water soluble, substituted triphenylphosphine.

16. The process according to claim 15, wherein the triphenylphosphine is represented by at least one of the following formulas:

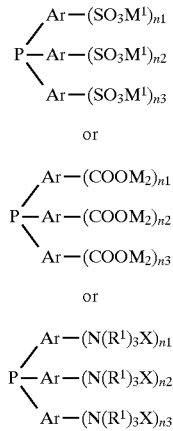

wherein Ar represents a phenyl group,
M$^1$ and M$^2$ represent a cationic organic or inorganic radical,
X represents an anionic organic or inorganic radical,
R$^1$ represents an C$_{1-18}$ aliphatic hydrocarbon group,
n1, n2 and n3 are the same or different and are each 0 or 1, and the sum of n1, n2 and n3 is at least 1.

17. The process according to claim 16, wherein SO$_3$M$^1$ is meta-substituted and COOM$_2$ or N(R$^1$)$_3$X are para-substituted at a phenyl group.

18. The process according to claim 15, wherein the mixture is prepared by isomerization of a 3-pentenoate.

19. The process according to claim 15, wherein the ratio of pentenoate mixture to water is between 10:90 and 90:10.

20. The process according to claim 15, wherein the water has a pH between 5.8 and 10.

21. The process according to claim 15, wherein the mixture comprises 3-pentenoate and 5–90% 4-pentenoate.

22. The process according to claim 21, wherein the mixture comprises 20–80% 4-pentenoate.

23. A process for preparing a linear aldehyde compound comprising the steps of:
   (i) forming an isomeric mixture of internally and terminally unsaturated organic compounds by isomerization of an internally unsaturated organic compound;
   (ii) directly hydroformylating said isomeric mixture in the presence of a catalyst which is capable of selectively catalyzing hydroformylation of the terminally unsaturated organic compound, under conditions such that a linear aldehyde compound is formed and there is substantially no hydroformylation of the internally unsaturated organic compound by the catalyst; and,
   (iii) recovering the linear aldehyde compound.

24. The process according to claim 23, which further comprises the step of recirculating any remaining isomeric mixture to step (i) and repeating steps (i) to (iii).

25. The process according to claim 23, wherein the catalyst is capable of catalyzing the hydroformylation of the terminally unsaturated organic compound at a reaction rate constant which is more than 100 times the reaction rate constant at which the catalyst catalyzes the hydroformylation of the internally unsaturated organic compound.

26. The process according to claim 23, wherein the internally unsaturated organic compound is a pentenoate.

27. The process according to claim 26, wherein the pentenoate is an alkyl pentenoate and the alkyl group therein contains between 1 and 8 carbon atoms.

28. The process according to claim 23, wherein the catalyst consists essentially of a platinum complex and a bidentate phosphine in a solvent, in the absence of SnCl$_2$ and protic acid.

29. The process according to claim 23, wherein the hydroformylation is carried out in the presence of water, rhodium and a water soluble, substituted triphenylphosphine.

30. The process according to claim 29, wherein the triphenylphosphine is represented by at least one of the following formulas:

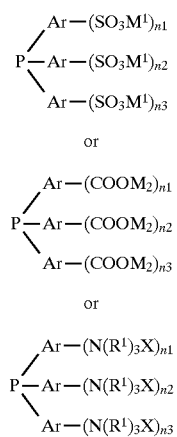

wherein Ar represents a phenyl group,
M$^1$ and M$^2$ represent a cationic organic or inorganic radical,
X represents an anionic organic or inorganic radical,
R$^1$ represents an C$_{1-18}$ aliphatic hydrocarbon group,
n1, n2 and n3 are the same or different and are each 0 or 1, and the sum of n1, n2 and n3 is at least 1.

31. The process according to claim 30, wherein SO$_3$M$^1$ is meta-substituted and COOM$_2$ or N(R$^1$)$_3$X are para-substituted at a phenyl group.

* * * * *

UNITED STATES PATENT AND TRADEMARK OFFICE
CERTIFICATE OF CORRECTION

PATENT NO.   : 5,811,589
DATED        : September 22, 1998
INVENTOR(S)  : TEUNISSEN et al.

It is certified that error appears in the above-identified patent and that said Letters Patent is hereby corrected as shown below:

Column 12, Claim 13, line 57, delete "R" and replace with --$R^1$--.

Signed and Sealed this

Fourth Day of April, 2000

Attest:

Q. TODD DICKINSON

*Attesting Officer*　　　　*Director of Patents and Trademarks*